US005609170A

United States Patent [19]
Roth

[11] Patent Number: 5,609,170
[45] Date of Patent: Mar. 11, 1997

[54] INTERPROXIMAL TOOTHBRUSH AND METHOD OF USE THEREOF

[76] Inventor: Edward S. Roth, 144-75 70th Rd., Kew Garden Hills, N.Y. 11367

[21] Appl. No.: 549,254

[22] Filed: Oct. 27, 1995

Related U.S. Application Data

[63] Continuation-in-part of Ser. No. 237,028, May 3, 1994, Pat. No. 5,507,646.

[51] Int. Cl.$^6$ ................................................ A61C 15/00
[52] U.S. Cl. ........................ 132/329; 132/321; 132/322; 132/200; 433/80; 15/167.1
[58] Field of Search .................................... 132/321, 322, 132/329, 200; 433/80, 215, 216; 15/167.1

[56] References Cited

U.S. PATENT DOCUMENTS

| | | | |
|---|---|---|---|
| 2,008,206 | 7/1935 | Grant | 132/329 |
| 3,672,378 | 6/1972 | Silverman | 132/329 |
| 4,878,508 | 11/1989 | Durbin | 132/329 |

*Primary Examiner*—Gene Mancene
*Assistant Examiner*—Pedro Philogene
*Attorney, Agent, or Firm*—Cobrin Gittes & Samuel

[57] ABSTRACT

An interproximal toothbrush and method for cleaning, irrigating and medicating a sub-gingival region with the same are disclosed. The interproximal toothbrush has outer and inner V-shaped portions having outer and inner working surfaces which form intersections at the distal ends from the spines, and bristles extending from the intersections which clean the deeper portions of the sub-gingival region between the teeth and gum. At least one aperture may be provided in at least one of the working surfaces such that irrigation fluid or a medicating, antibacterial or other cleaning agent may be dispensed from the aperture and be guided by the bristles to the sub-gingival region.

8 Claims, 5 Drawing Sheets

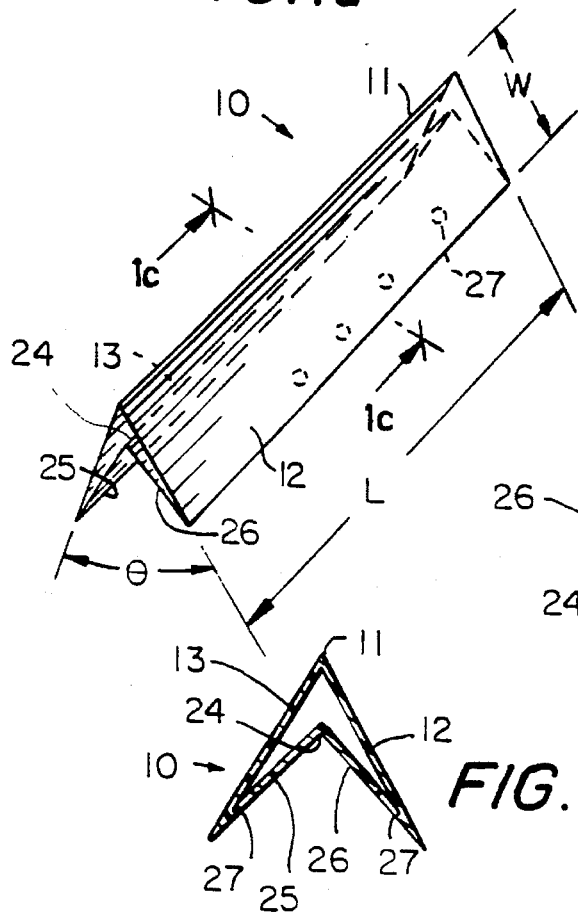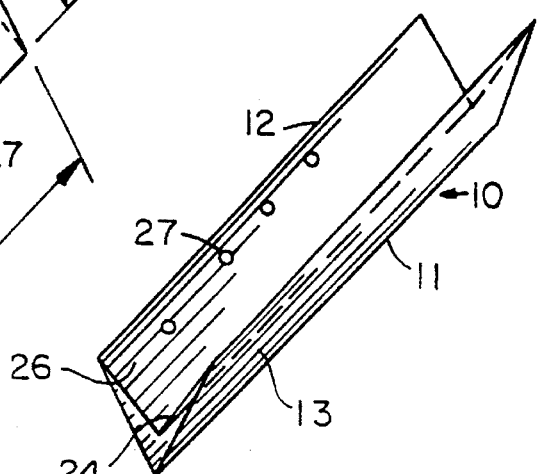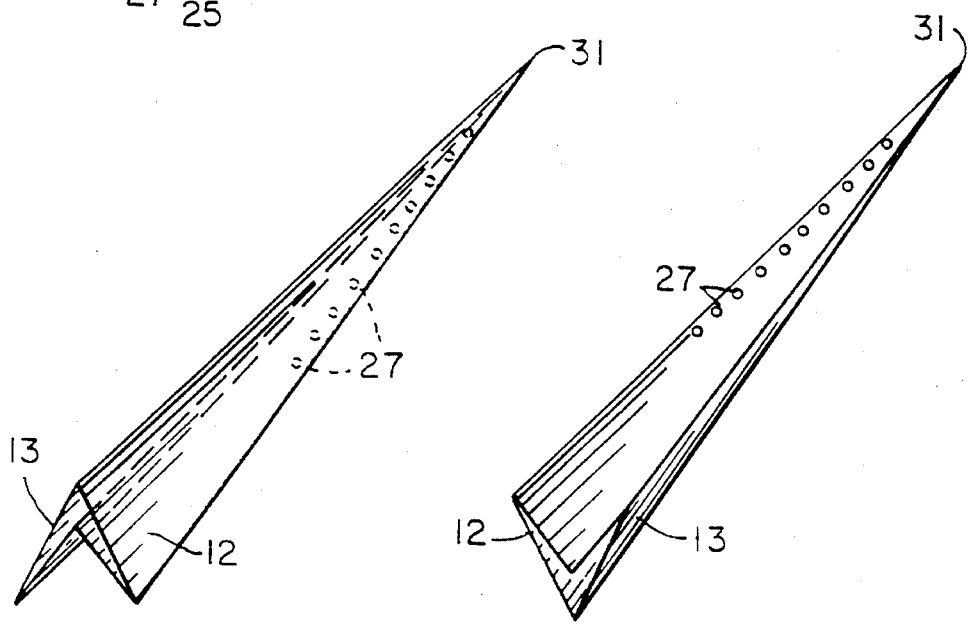

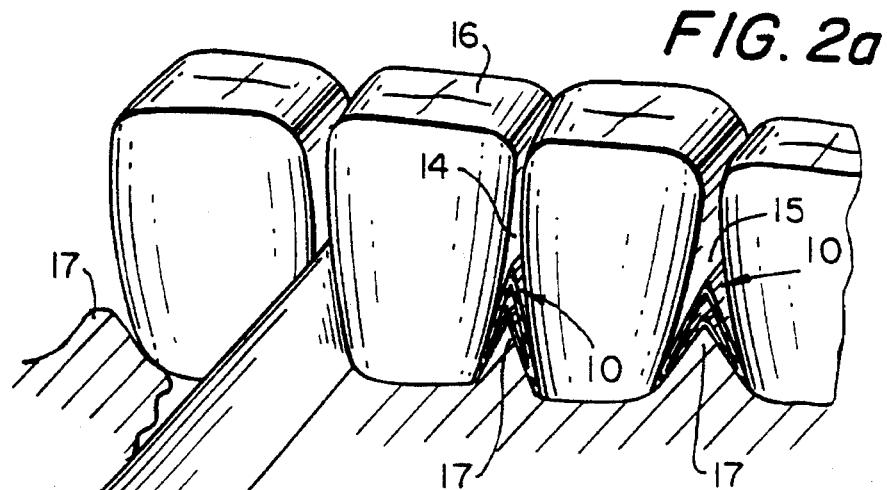
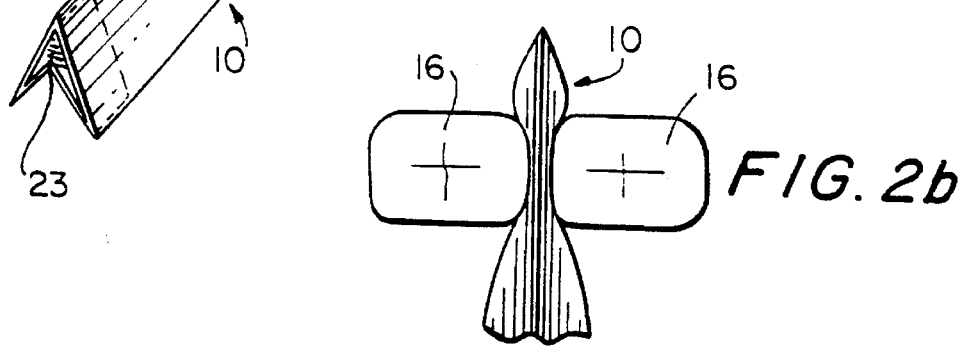
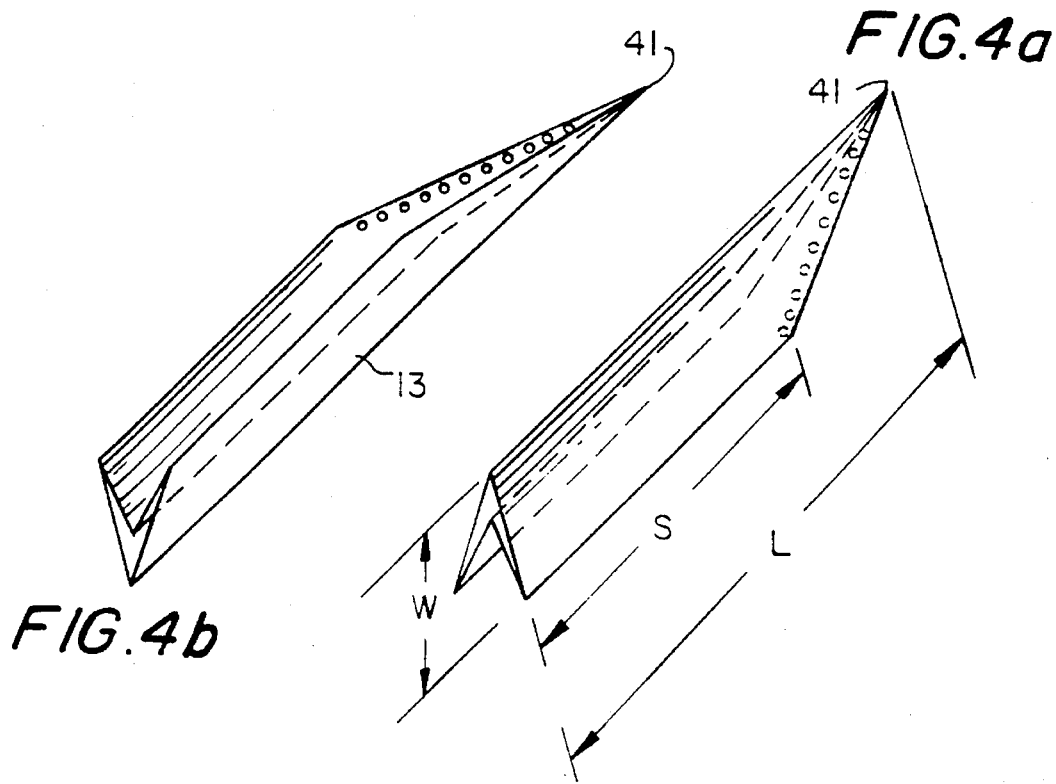

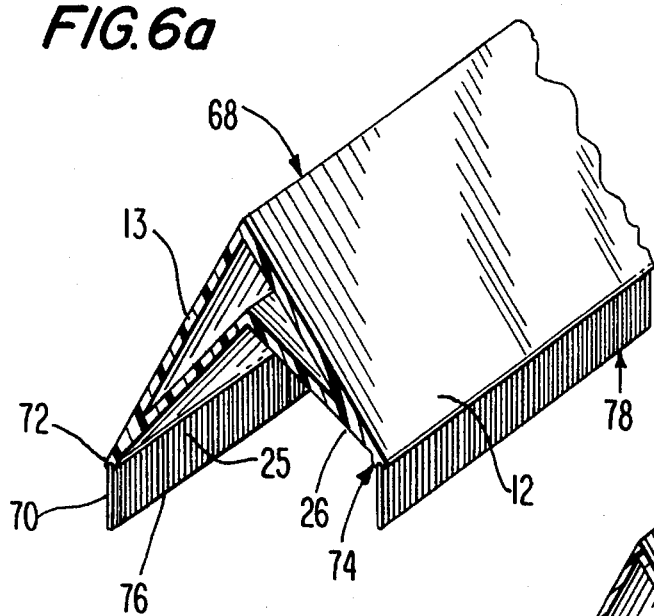
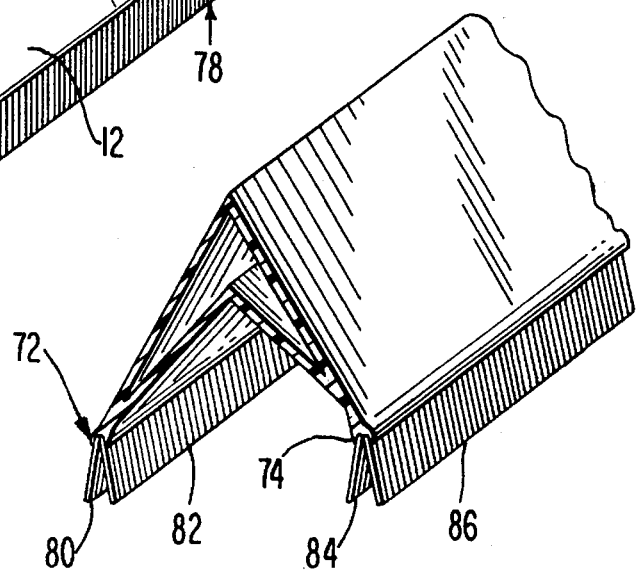
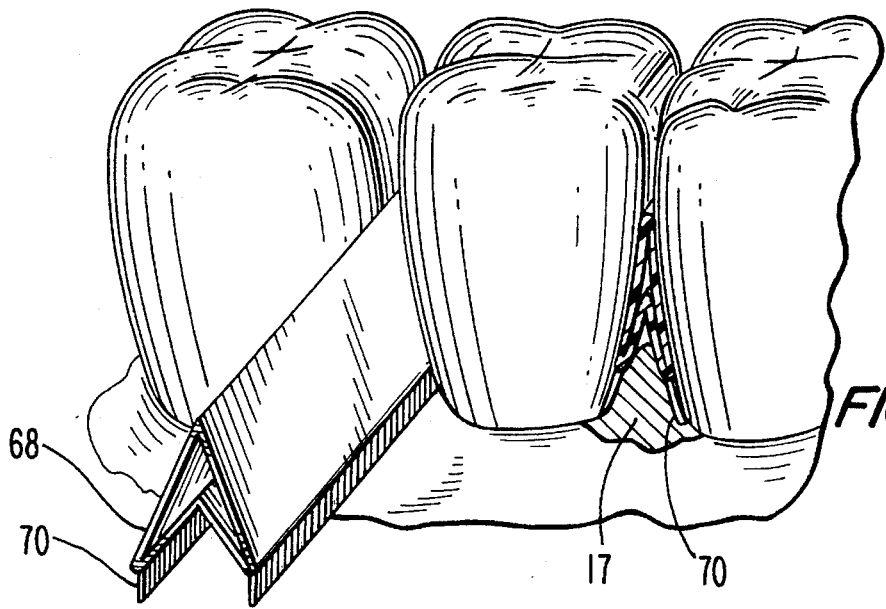

INTERPROXIMAL TOOTHBRUSH AND METHOD OF USE THEREOF

This application is continuation-in-part of application Ser. No. 08/237,028, filed May 3, 1994, now U.S. Pat. No. 5,507,646.

BACKGROUND OF THE INVENTION

1. Field of the Invention

The invention pertains to the field of oral hygiene and more particularly to the irrigating, medicating and cleansing of the sub-gingival area extending from the gingival crest to the attachment apparatus at the base of the gingival pocket or gingival sulcus.

2. Description of the Prior Art

A periodontal interproximal region is formed by two contacting teeth which create an embrasure space apical to the contact area and a sluce-way coronally. Within the embrasure space are located the gingival papilla, whose mesial and distal surfaces form the gingival sulcus. The sulcus has an integral gingival surface composed of non-keratinized unattached gingiva and terminates at the beginning of the tooth's attachment apparatus. This area, beginning at the gingival margin and extending to the base of the attachment apparatus, including the mesial and distal aspects thereof, is referred to herein as the "sub-gingival region". In healthy gingiva the distance from the coronal gingival margin to the attachment apparatus is generally between 1 and 3 millimeters. Because of the shape of the periodontal interproximal area, food and bacteria may accumulate between the teeth and penetrate deep into the gingival sulcus. If the bacteria are allowed to remain in the sulcus, a complex structure (sulcular flora) forms and the tissue becomes inflamed. This inflammation of the gingival tissue is associated with gingival bleeding and halitosis and is called gingivitis. If any of the known periopathic bacteria are part of the sulcular flora, the attachment apparatus becomes damaged and a complex immuno-pathological event occurs that causes continued loss of attachment, osteoclasia and periodontal pocket formation. This condition is called periodontitis which is the leading cause of tooth loss in adults. Numerous studies have shown that periodontal disease can be prevented or halted when bacteria are not present or viable in the periodontal pocket. If bacterial deposits at the depths of the periodontal pocket could be neutralized every day, the periodontal attachment apparatus could be maintained and further breakdown would not occur. The problems of reaching deep into the periodontal pocket are many, the most limiting of which are:

the teeth and interproximal areas extend deep into a small oral cavity;

the tongue limits the space of operation;

tight tooth contact does not allow easy passage of an irrigating device in a coronal apical direction;

access to the depths of the periodontal pocket is inhibited by papillary gingiva filling the region;

the irrigation device is too large to enter the depths of the periodontal pocket;

space between adjacent sub-gingival pockets is hour glass shaped;

gingival plaque adheres tightly to the sub-gingival surface;

hard deposits (calculus) on tooth interfere with penetration; and it is difficult to penetrate the periodontal pocket without damaging hard or soft tissue.

A tooth brush, when properly used, is adequate for cleaning the facial and lingual aspects of the gingival sulcus. The bristles of the tooth brush, however, are deflected by the papilla and do not penetrate into the periodontal pocket or the mesial and distal aspects of the sulcus when the tooth brush is used against the facial or lingual surfaces. Access by the bristles to the interproximal papilla is also inhibited when in contact with the occlusal surfaces. Further, the bristles of the tooth brush are sufficiently hard to erode and lacerate the papillary tissue should sub-gingival penetration be forced. Additionally, the tooth brush is bulky and difficult to maneuver in the mouth, therefore limiting precision and pinpoint cleansing.

A curette, a metallic device which is spoon shaped for adapting to the tooth surface and having knife-like cutting edges, is presently available for reaching the sub-gingival region. Such a device, however, is difficult to use and may only be used by a professional. Even when properly used, the blade surface opposite the tooth removes the internal subgingival tissue surface, thus lacerating the tissue to cause bleeding and, almost always, gingival shrinkage or recision. These devices are rigid and different curettes must be used in the same oral cavity due to oral cavity anatomical variations. Further, this rigidity prevents the delivery of antibacterial agents during its usage.

Gum massagers, interdental stimulators and rubber tips utilized in the prior art for interproximal cleaning are too bulky to penetrate into the sub-gingival region. These device are designed to stimulate the gingiva and to clean supragingivally (above the gum line). They are not flexible and rely on compression to achieve close contact with the teeth in the interproximal space. The combination of bulk and inflexibility generally prevents reaching the mesial lingual and distal lingual aspects of the tooth. Further, their bulk prevents deep cleaning of the sulcus or the pocket and may actually compress food and bacteria into those areas. In addition, these devices do not account for the presence of the papilla and, when inserted, deform and squeeze the papilla tightly against the tooth surface making it impossible to pass fluids into sub-gingival region.

Another device of the prior art used for interproximal cleaning is known as a periodontal pocket cleaner. This is a wooden apparatus which may splinter when forced into the interproximal area. Further, it is not flexible and can not adapt to the various interproximal tooth configurations which are encountered in an oral cavity. This device tapers to a point for insertion into the pocket. When the device is not used precisely the point may lacerate gingiva or sulcus. Cleaning is performed with a scooping action that opens the gingival sulcus and effective cleaning of the mesial lingual or distal lingual aspects of the sulcus with this device is difficult.

Another cleaning device available to the public is the well known dental floss. This thread like cleaning aid can reach the depth of the gingival sulcus and pocket and adequately clean that area. The oral cavity, however, may create serious floss access problems. Very often the dental floss must pass through contacting teeth, breaking in the process, thus providing further frustration. To pass through contacting teeth the floss must be taut and appreciable force must be applied. At times the floss snaps past the contact area to incise the gingival papilla and mutilate the tissue with considerable pain to the individual applying or having the floss applied. Moreover, it cannot deliver fluids to the sub-gingival area effectively.

Still another device of the prior art comprises a wire shaft with a multiplicity of bristles attached thereto, having the trademark PROXABRUSH. This apparatus is relatively bulky, does not fit between many teeth, and is difficult to negotiate in the oral cavity. In use, the bristles rest on the top of the papilla and are passed back and forth between teeth to cleanse the interproximal region. This action causes the papilla to erode and the penetration of the bristles within the gingival sulcus is not deep, thereby providing only partial cleansing of the interproximal area. For the device to penetrate the interproximal region, the bristle supporting wire must be thin. Thus, the wire is not sufficiently rigid or strong and distorts and often breaks in use, leaving the wire and bristles between the teeth.

Toothpicks are disclosed in U.S. Pat. No. 4,577,649 to Shimenkov (the '649 patent), the entire disclosure of which is incorporated herein by reference. In one embodiment of the '649 patent shown in FIG. 3 therein, two side faces incline toward one another so as to form an acute angle therebetween. Another embodiment shown in FIG. 4 of the '649 patent contains a third face directly connecting the two outer edges of the two side faces, thereby forming a hollow area inside. As is readily seen in FIG. 1 of the '649 patent, both embodiments discussed above are configured such that they enter and treat the gap between the teeth supragingivally, i.e., above the gum tissue. Moreover, when medication or toothpaste is dispensed from the side faces of the device, it is dispensed directly to the teeth and above the gum line. U.S. Pat. No. 4,805,646 to Shimenkov (the '646 patent), also incorporated herein by reference, discloses a toothpick having two body portions forming an acute angle which are movable relative to one another and a spongy inner layer therebetween. The spongy inner layer is inconveniently attached by gluing to the inside of the two body portions.

It is an object of the present invention to provide a method of cleaning the subgingival region.

It is an object of the present invention to provide a method of cleaning and irrigating the sub-gingival region.

It is a further object of the present invention to provide a method of neutralizing plaque and bacteria through the dispensing of medicating or antibacterial agents into the sub-gingival region.

It is a further object of the present invention to provide a method of cleaning, irrigating or medicating the sub-gingival region wherein all areas of the oral cavity are accessed.

It is still a further objective of the present invention to provide a method of cleaning, irrigating or medicating the subgingival region wherein the sub-gingival periodontal irrigator does not deform.

It is still a further objective of the present invention to provide a method of cleaning, irrigating or medicating the sub-gingival region wherein the sub-gingival periodontal irrigator is guided by the dental anatomy to access the deepest aspects of the sub-gingival region.

It is still a further objective of the present invention to provide a method of cleaning, irrigating or medicating the sub-gingival region wherein an interproximal toothbrush guides the bristles thereof into the deepest aspects of the sub-gingival region.

SUMMARY OF THE INVENTION

The present invention involves cleansing of the sub-gingival region by inserting into the periodontal interproximal region a sub-gingival periodontal cleaner having two V-shaped working portions forming a hollow space therebetween. The V-shaped working portions each have a spine and two working surfaces which generally form an acute angle therebetween. The two V-shaped portions intersect at the distal ends of the working surfaces from the spines. The V-shaped working portions are made of plastic material and may be tapered for easy access to the interproximal area. The sub-gingival periodontal cleaner is guided by the dental anatomy to straddle the papillary gingiva to cleanse the sub-gingival region.

In the preferred embodiment, the sub-gingival periodontal cleaner has at least one aperture in at least one of the inner V-shaped working surfaces. For ease of discussion, a sub-gingival periodontal cleaner with apertures is referred to as a sub-gingival periodontal irrigator. Irrigation fluid or antibacterial or medicating agent is placed within the hollow area of the sub-gingival periodontal irrigator prior to use. When the device is inserted into the periodontal interproximal region between two adjacent teeth, the resulting constriction of the device forces the irrigation fluid or medicating agent through the at least one aperture to the sub-gingival region. The contents may also be dispensed by squeezing the sub-gingival periodontal irrigator. Most preferably, the at least one aperture is disposed in at least one of the inner working surfaces at or near the distal end from the inner spine. Antibacterial agent, medicating agent or irrigation fluid contained within the hollow portion of the irrigator may thus be dispensed directly to the marginal gingiva below the gum line.

Insertion of the sub-gingival periodontal cleaner and/or irrigator into the periodontal interproximal region may be facilitated by use of a holder.

Another embodiment of the sub-gingival periodontal cleaner is provided which has bristles on the distal ends of the working surfaces. The bristles extend downward from each distal end. When the sub-gingival periodontal cleaner with bristles is inserted into an interproximal area, the bristles clean the deepest aspects of the sub-gingival pocket or sulcus. The sub-gingival periodontal cleaner with bristles thus functions as an interproximal toothbrush. Contact of the deepest aspects of the sub-gingival pocket or sulcus with bristles alleviates or prevents laceration of the tissue.

When at least one aperture is present in an interproximal toothbrush, the bristles clean the pocket or sulcus area and irrigation fluid or antibacterial, medicating or other cleaning agent may be dispensed from at least one aperture of the device.

BRIEF DESCRIPTION OF THE DRAWINGS

FIGS. 1a and 1b are views of an embodiment of the sub-gingival periodontal irrigator of the present invention wherein surfaces of the device have parallel longitudinal edges.

FIG. 1c is a cross-sectional view of the sub-gingival periodontal irrigator of FIG. 1a along the lines 1c.

FIG. 2a is a pictorial representation of an insertion of the sub-gingival periodontal irrigator of the present invention into a periodontal interproximal area and illustrates the adaptability of the device to the interproximal area configuration.

FIG. 2b is an occlusal view of the sub-gingival periodontal irrigator of the present invention positioned between two teeth.

FIGS. 3a and 3b are views of an embodiment of the sub-gingival periodontal irrigator of the present invention wherein surfaces of the device have longitudinal edges that taper to a point.

FIGS. 4a and 4b are views of an embodiment of the sub-gingival periodontal irrigator of the present invention wherein surfaces of the device have parallel longitudinal edges for a predetermined distance and thereafter taper to a point.

FIGS. 6a and 6b are views of embodiments of an interproximal toothbrush.

FIG. 7 is a pictorial representation of an insertion of the interproximal toothbrush of FIG. 6a into the interproximal area.

DESCRIPTION OF THE PREFERRED EMBODIMENTS

Figure 5A:
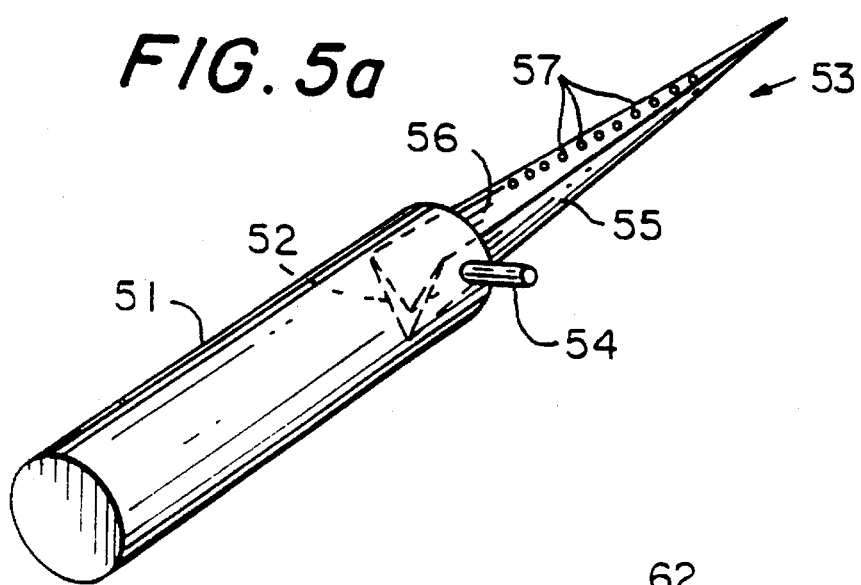
FIGS. 5a and 5b are pictorial representations of the sub-gingival irrigator of the present invention inserted in dispenser holders.

A sub-gingival periodontal cleaner is provided which safely and conveniently permits the cleansing of the sub-gingival region, particularly the mesial and distal aspects below the gum line. The sub-gingival periodontal irrigator is the preferred embodiment of the sub-gingival periodontal cleaner in which the cleaner has at least one aperture to permit the dispensing of an irrigating, medicating or antibacterial agent. The sub-gingival periodontal cleaner thus encompasses embodiments with and without apertures.

A sub-gingival periodontal irrigator 10 in accordance with the present invention is illustrated in FIGS. 1a and 1b. It consists of an outer and inner V-shaped working portion, each consisting of flexible plastic material. The outer V-shaped working portion is shaped to establish an outer spine 11 wherefrom first and second outer working surfaces 12 and 13 extend to form a V shape having and angle Θ, which is generally an acute angle in the working configuration and generally about 45° in the non-working configuration. The inner V-shaped working portion, made from the same or another suitable plastic material or the like, having inner spine 24 and inner working surfaces 25 and 26, is coupled with the outer working surfaces 12 and 13 in a manner to establish a hollow space between the outer and inner V-shaped working portions. The V-shaped working portions are coupled such that the distal ends of working surfaces 13 and 25, and 12 and 26 are connected.

The material may be thermoplastic, such as commercially available polypropylene or polyethylene, which is flexible or resilient yet sufficiently stiff to maintain a straight outer spine 11 along the longitudinal axis while and after the sub-gingival periodontal irrigator 10 is guided into the interproximal region. The flexibility or resiliency of the sub-gingival periodontal irrigator 10 permits the dental anatomy to guide it into function as it is inserted into the interproximal region and permits the angle e to vary in conformance with the configuration of the periodontal interproximal region. This adaptability is illustrated in FIG. 2a wherein a cross-section of an inserted sub-gingival periodontal irrigator 10 is shown in a relatively narrow interproximal region 14 and a relatively broad interproximal region 15. Generally, the interproximal region angular variation is in the range between 18° and 48°, the angle for each region being determined by the interproximal space and established by the forces exerted on the cleaner by the teeth 16 and papillary gingiva 17. It should be apparent, however, that in almost all situations the sub-gingival periodontal irrigator must be sufficiently flexible or resilient to assume an hour glass configuration in the occlusal plane as shown in FIG. 2b.

A triangular plug 23, shown in FIG. 2a, may be inserted between the outer and inner working surfaces on the external end of the sub-gingival periodontal irrigator 10 to maintain the V shape for the entire device. Though the V shape is maintained, it should be recognized that an angular transition takes place between the external end and the working area. This angular transition creates working forces for the interproximal cleaning. The working surfaces 12 and 13 may be finished to provide a brush like texture to clean the sub-gingival region.

The distal ends of the working surfaces from the spines are thus adapted to remove food, bacteria and plaque from the sub-gingival region by making contact between the marginal gingiva below the gum line and the teeth. In this way the sub-gingival periodontal cleaner or irrigator is well suited to clean the sub-gingival region.

Irrigation fluid or medicating or antibacterial agent may be inserted into the hollow space between the outer and inner working surfaces prior to use. A predetermined amount or unit dose may be readily inserted into the hollow area given the volume of this area. By use of triangular plug 23, the space between the two outer and inner V-shaped working surfaces may be sealed. A second slidable plug may be diametrically provided. It will be appreciated that tubing or other means of continuous irrigation may be connected to the hollow space to provide a continuous supply of irrigation fluid. At least one aperture 27 may be present in the inner and/or outer working surfaces of the V shaped device from which irrigation fluid or medicating or antibiotic agent is dispensed when the sub-gingival periodontal irrigator is squeezed between the teeth or by a force applied at the external end. Where the apertures are placed would depend on the area to be medicated and/or irrigated. Preferably, apertures are located in at least one of the inner working surfaces at the distal end from the inner spine. Having the apertures placed in this area readily permits the irrigation and/or medication of the gingival pocket or sulcus below the gum line. Inner surfaces 25 and 26 are smooth to minimize discomfort and to facilitate dispensing the irrigation fluid or medicating or antibiotic agent to the sub-gingival region. Alternatively, these surfaces may be textured to facilitate cleaning of the tissue. The length L of the sub-gingival periodontal irrigator may be one and one-half (1-½) inches and the width W of the working surface may be between three and seven millimeters.

Entry into the interproximal space by the working surfaces 12 and 13 of the sub-gingival periodontal irrigator 10 may be facilitated by tapering these surfaces to a point 31 in an embodiment of the invention shown in FIGS. 3a and 3b. The angle at which the device is tapered may be varied as shown in FIGS. 4(a) and 4(b). Since sulcular and pocket depth vary, the tapering will facilitate complete cleaning by automatically adjusting the width of the working surface as needed. Thus entry is facilitated and complete cleaning is accomplished with a reasonable depth of penetration.

FIGS. 6a and 6b are views of embodiments of a subgingival periodontal cleaner having bristles at the distal ends of the working surfaces. The bristles clean the interproximal periodontal area between the marginal gingiva and the teeth below the gum line. Accordingly, the device is also called an interproximal toothbrush. In interproximal toothbrush 68, bristles 70 extend downward from the intersections 72 and 74 of the distal ends of working surfaces 13 and 25 and of working surfaces 12 and 26, respectively. In FIG. 6a, one row 76 of bristles 70 extends from intersection 72 and one row 78 of bristles 70 extends from intersection 74. In FIG. 6b, 2 rows 80 and 82 extend from intersection 72 and 2 rows 84 and 86 extend from intersection 74. The rows can be staggered from each other as shown or closer and less well defined. The number of rows can further vary. The bristles are similar to those used in toothbrushes and are typically made of nylon. They are generally about 1–3 mm long. About a 2 mm bristle length is preferred. The bristles are typically soft and spaced close together. The placement and firmness of the bristles should be such that a sufficiently soft surface contacts the sub-gingivat tissue. The bristles therefore alleviate or prevent laceration of the gum tissue in the sensitive areas of the deepest aspects of the sub-gingival pocket or sulcus.

FIG. 7 is a pictorial representation of an insertion of the interproximal toothbrush of FIG. 6a into the interproximal area. Interproximal toothbrush 68 is depicted straddling the papillary gingiva 17 both in full view and in cross-section. Bristles 70 are shown below the gum line next to the teeth. The interproximal toothbrush thus straddles the apex of the papilla and guides the bristles into the sulcus or pocket area. The bristles reach the depth of the periodontal sulcus or pocket and sweep the bacterial plaque and debris out of the area.

Figure 8A:
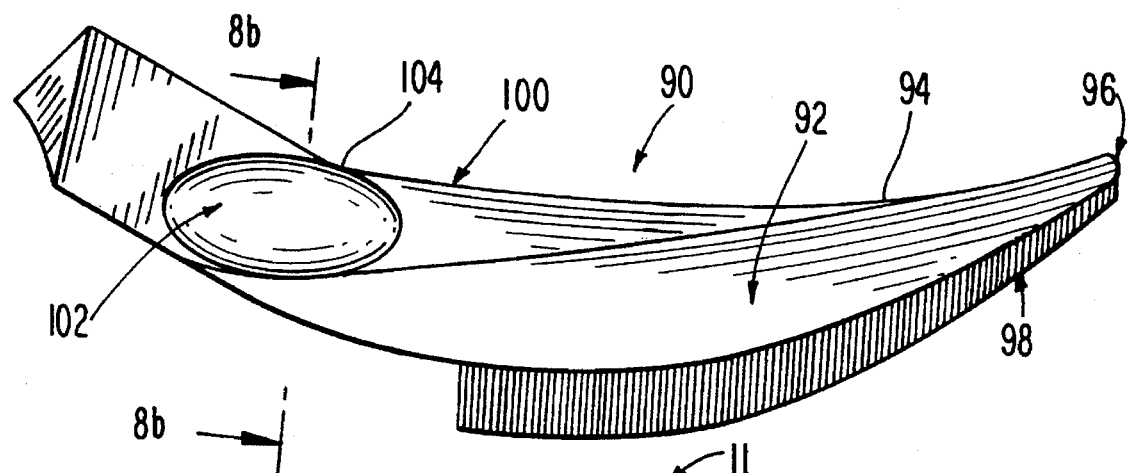
FIG. 8a is a side view of a preferred embodiment of an interproximal toothbrush of the present invention having a pitched shape.

FIG. 8a is a side view of a preferred embodiment of an interproximal toothbrush of the present invention having a pitched shape. Interproximal toothbrush 90 has a pitched or arced shape where working surfaces 92 and 94, not seen, are tapered toward each other such that the front of the device has a blunt tip 96. The bristles are graduated such that shorter bristles closer to the front of the device towards blunt tip 96 first contact sub-gingival tissue followed by longer bristles toward the back end. Graduated bristles are preferred. The pitched shape as well as the blunt tip effectively avoid entrance and exit tears of the gingival tissue. The distal ends of the working surfaces closer to the front of the device may not have bristles. This area provides a guidance arc 98, which in conjunction with the blunt tip 96, provides a structure with which to guide the bristles into place. Blunt tip 96 in particular avoids injury to the papillary gingiva.

Blunt tip 96 is the intersection point of the spine of the outer V-shaped portion where the two outer working portions arc towards each other and meet. The inner V-shaped working portion (not shown) is somewhat recessed. The inner V-shaped working portion may begin where the guidance arc ends and the bristles begin. Solid handle 100 is depicted at the back end of the interproximal toothbrush opposite blunt tip 96. Finger grasp areas 102 and 104, not seen, are concave depressions in solid handle 100 which permit comfortable control of the device.

Figure 8B:
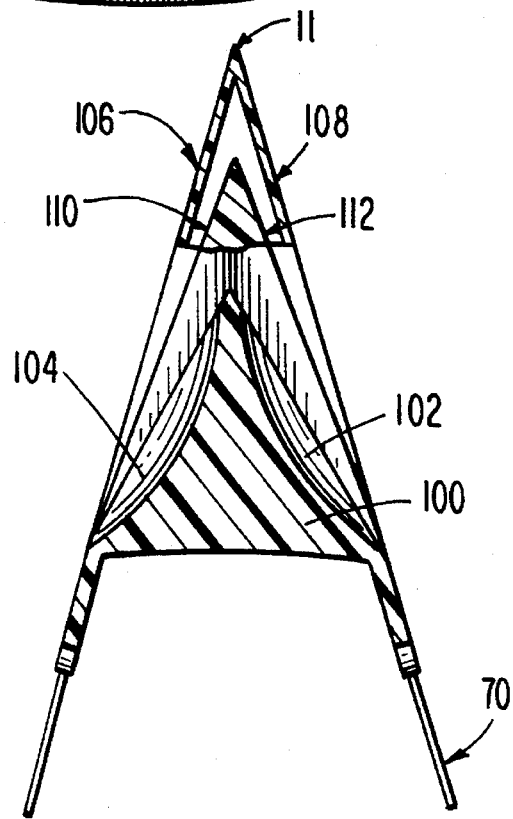
FIG. 8b is a cross sectional view of the interproximal toothbrush of FIG. 8a taken along the lines of 8b—8b with a portion broken away and in cross-section.

FIG. 8b is a cross sectional view of the interproximal toothbrush of FIG. 8a taken along the lines 8b—8b with a portion broken away and in cross-section. Finger grasp areas 102 and 104 and solid handle 100 are shown in accordance with the view directly along lines 8b—8b. Portions shown above this area are visible along the lines 8b—8b above solid handle 100. The broken away portion depicts spine 11, and outer working surfaces 106 and 108 and inner working surfaces 110 and 112 forming a hollow space therebetween.

Preferably, the interproximal toothbrush contains apertures as described with respect to the sub-gingival periodontal irrigator. Antibacterial, medicating or other tooth and/or gum cleaning agent or irrigation fluid can similarly be delivered from such apertures. These agents are contained within the hollow area of the device and are extruded from the apertures while the device is in the interproximal space. The agent is then guided by the bristles to enter the deeper regions of the pocket or sulcus.

Greater control of the sub-gingival periodontal cleaner or interproximal toothbrush may be provided by supporting the sub-gingival periodontal cleaner or irrigator in a holder. Refer now to FIG. 5a, wherein a holder 51 which may be a wooden cylinder with a V-notch 52 at one end that is sufficiently deep to hold a sub-gingival periodontal irrigator 53 with its axis in parallel with or in coaxial alignment with the axis of the holder 53 is shown. A slidable plug 54 may be positioned in the holder at the V notch end for applying a squeezing force to the sub-gingival periodontal irrigator 53 to dispense the irrigation fluid or medicating or antibacterial agent contained between outer working surfaces 55 and inner working surfaces 56 of the sub-gingival periodontal irrigator 53 through apertures 57.

Figure 5B:
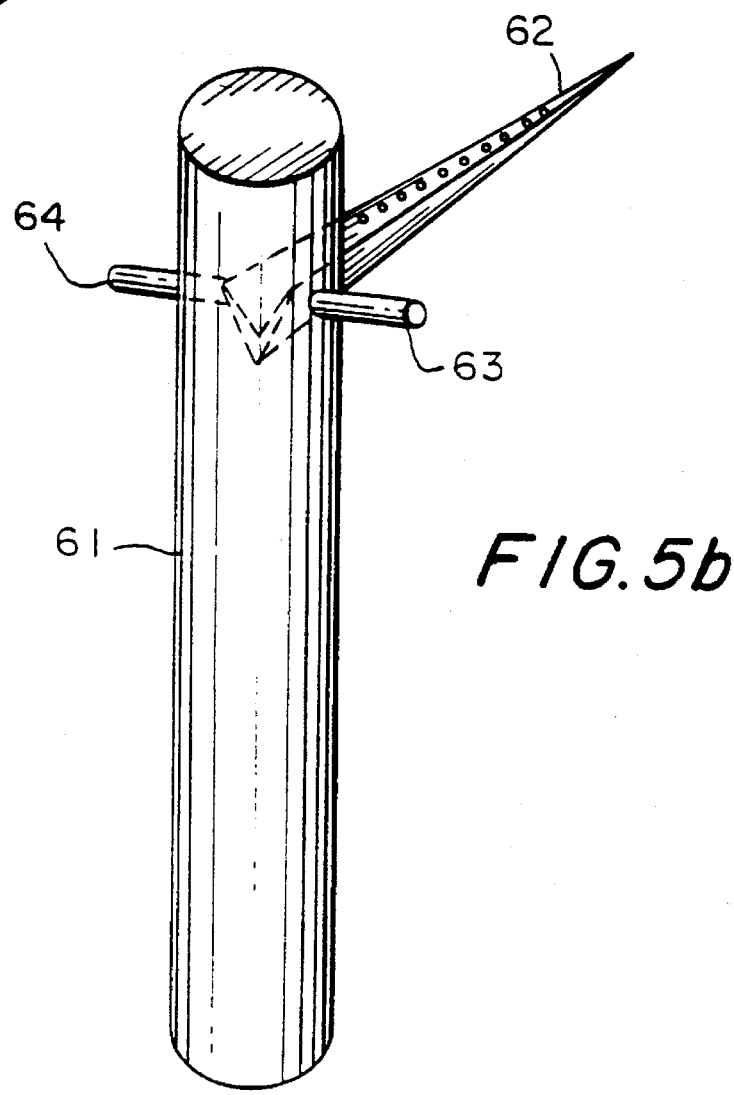

In FIG. 5b a holder 61 with a V notch positioned to hold a sub-gingival periodontal irrigator 62 with its axis perpendicular to the axis of the holder is shown. First 63 and second 64 slidable plugs may be diametrically located, as described above, for dispensing the irrigation fluid or antibacterial or medicating agent contained between the outer and inner working surfaces of the sub-gingival periodontal irrigator 62.

While the invention has been described in its preferred embodiments, it is to be understood that the words which have been used are words of description rather than of limitation and that changes within the purview of the appended claims may be made without departure from the true scope and spirit of the invention in its broader aspects.

What is claimed is:

1. A method of cleaning a sub-gingival region comprising:
   inserting an interproximal toothbrush into a periodontal interproximal region, said interproximal toothbrush having outer and inner V-shaped working portions of flexible material, where said outer V-shaped working portion has outer working surfaces intersecting to establish an outer spine, said inner V-shaped working portion having inner working surfaces intersecting to establish an inner spine, where said outer and inner working surfaces form intersections at the distal ends of said working surfaces from said spines and where bristles extend from said intersections; and
   contacting the periodontal area between the marginal gingiva and the teeth below the gum line with said bristles.

2. A method as claimed in claim 1 in which said contacting occurs with shorter length bristles followed by bristles of gradually longer length.

3. A method as claimed in claim 1 in which said inserting an interproximal toothbrush is facilitated by holding finger grasp areas of a handle at the rear portion of said interproximal toothbrush.

4. A method of cleaning a sub-gingival region comprising:
   inserting a guidance arc of an interproximal toothbrush having a pitched shape into a periodontal interproximal region, said interproximal toothbrush having outer and inner V-shaped working portions of flexible material, where said outer V-shaped working portion has outer working surfaces intersecting to establish an outer spine, said inner V-shaped working portion having inner working surfaces intersecting to establish an inner spine, where said outer and inner working surfaces form intersections at the distal ends of said working surfaces from said spines and where bristles extend from said intersections after said guidance arc starting with shorter bristles followed by gradually longer bristles; and contacting the periodontal area between the marginal gingiva and the teeth below the gum line with said bristles.

5. A method of cleaning and irrigating a sub-gingival region comprising:

adding irrigation fluid to a hollow space between outer and inner V-shaped working portions of flexible material of an interproximal toothbrush, where said outer V-shaped working portion has working surfaces intersecting to establish an outer spine, said inner V-shaped working portion having inner working surfaces intersecting to establish an inner spine, where said outer and inner working surfaces form intersections at the distal ends of said working surfaces from said spines, such that said hollow space is provided between said outer V-shaped working portion and said inner V-shaped working portion and bristles extend from said intersections;

inserting said interproximal toothbrush into a periodontal interproximal region:

contacting the periodontal area between the marginal gingiva and the teeth below the gum line with said bristles; and dispensing irrigation fluid from at least one aperture in at least one of said working surfaces to said sub-gingival region.

6. A method of cleaning and medicating a sub-gingival region comprising:

adding medicating, antibacterial or other cleaning agent to a hollow space between outer and inner V-shaped working portions of flexible material of an interproximal toothbrush, where said outer V-shaped working portion has working surfaces intersecting to establish an outer spine, and said inner V-shaped working portion having inner working surfaces intersecting to establish an inner spine, where said outer and inner working surfaces form intersections at the distal ends of said working surfaces from said spines such that said hollow space is provided between said outer V-shaped working portion and said inner V-shaped working portion and where bristles extend from said intersections;

guiding said interproximal toothbrush into a periodontal interproximal region;

contacting the periodontal area between the marginal gingiva and the teeth below the gum line with said bristles; and dispensing said medicating, antibacterial or other cleaning agent from at least one aperture in at least one of said working surfaces to said sub-gingival region.

7. An interproximal toothbrush for cleaning and irrigating a periodontal interproximal region comprising:

(a) outer V-shaped working portions of flexible material which intersect to establish an outer spine;

(b) inner V-shaped working portions of flexible material which intersect to establish an inner spine;

(c) intersections formed by the meeting of the distal ends of said outer and inner working surfaces from said spines;

(d) bristles extending from said intersections, (e) at least one aperture in at least one of said working surfaces, where said outer and inner working portions and said intersections thereof are disposed so as to form a hollow space therebetween capable of holding irrigation fluid therein.

8. An interproximal toothbrush for cleaning and medicating a periodontal interproximal region comprising:

(a) outer V-shaped working portions of flexible material which intersect to establish an outer spine;

(b) inner V-shaped working portions of flexible material which intersect to establish an inner spine;

(c) intersections formed by the meeting of the distal ends of said outer and inner working surfaces from said spines;

(d) bristles extending from said intersections, (e) at least one aperture in at least one of said working surfaces, where said outer and inner working portions and said intersections thereof are disposed such as to form a hollow space therebetween capable of holding medicating, antibacterial or other cleaning agent therein.

* * * * *